| United States Patent [19] | [11] Patent Number: 4,530,829 |
| Abe | [45] Date of Patent: Jul. 23, 1985 |

[54] HAIR TREATMENTS

[75] Inventor: Yoshiaki Abe, Tokyo, Japan

[73] Assignee: Kao Corporation, Tokyo, Japan

[21] Appl. No.: 416,665

[22] Filed: Sep. 10, 1982

[30] Foreign Application Priority Data

Sep. 14, 1981 [JP] Japan ................. 56-144992

[51] Int. Cl.³ ............. A61K 7/06; A61K 7/08; A61K 7/11
[52] U.S. Cl. ................. 424/70; 424/DIG. 1; 424/DIG. 2; 424/71
[58] Field of Search ........................... 424/70

[56] References Cited

U.S. PATENT DOCUMENTS

| 3,904,748 | 9/1975 | Eckert et al. | 424/70 |
| 4,279,996 | 7/1981 | Yoshioka et al. | 424/70 |

FOREIGN PATENT DOCUMENTS

| 2262375 | 6/1974 | Fed. Rep. of Germany | 424/245 |
| 2438662 | 5/1980 | France | 424/309 |
| 1196570 | 7/1970 | United Kingdom | 424/177 |

*Primary Examiner*—Dale R. Ore
*Attorney, Agent, or Firm*—Oblon, Fishner, Spivak, McClelland & Maier

[57] ABSTRACT

Disclosed herein is a hair treatment which comprises the following two ingredients (A) and (B): (A) polyphenol compound ... 0.001–5.0 wt % (B) chelating agent ... 0.01–5.0 wt %. Also disclosed a hair treatment which comprises, in addition to the ingredients (A) and (B), the third ingredient (C): (C) At least one decomposition derivative of keratin material selected from the group consisting of (1) hydrolysates of keratin material, (2) alkali salts of decomposition products obtained by oxidation of keratin material, and (3) alkali salts of derivatives at the thiol groups of decomposition products obtained by reduction of keratin material ... 0.05–10.0 wt %. The hair treatment according to this invention can prevent proteins from eluting from hair and restore appropriate degrees of resiliency and flexibility of the hair which have once been lost by treatments for beauty care.

13 Claims, No Drawings

HAIR TREATMENTS

BACKGROUND OF THE INVENTION

1. Field of the Invention

This invention relates to hair treatments and more particularly, to hair treatments comprising polyphenol compounds and chelating agents with or without keratin derivatives of the specific type.

2. Description of the Prior Art

Various treatments have ordinarily been applied to hair for beauty care, causing the hair to be damaged. For instance, the beauty treatments such as washing with shampoo, drying with dryer, cold perm, hair dye, hair bleach and the like give chemically and physically damage to the hair due to the elution of proteins therefrom, so that the strength of the hair is lowered and the flexibility is lost, causing split ends or broken hairs.

In order to prevent the hair from being damaged, it is the usaul practice to use hair rinses and hair treatments which contain quaternary ammonium salts. However, this practice is certainly effective in softening the hair, preventing the hair from being statically charged but proteins which have once been lost from the hair are not restructured and thus only a transient effect is expected.

SUMMARY OF THE INVENTION

We have made an intensive study to develop hair treatments exhibiting an excellent hair protecting effect and an excellent style-forming and retaining ability. As a result, it has been found that hair treatments using polyphenol compounds and chelating agents in combination can prevent proteins from eluting from hair to potentially protect the hair and restore appropriate degrees of resiliency and flexibility of the hair which have once been lost by treatments for beauty care, coupled with excellent style forming and retaining ability.

Moreover, when a specific type of keratin derivative is further added to the hair treatment, the above effects were found to be further improved.

That is, according to one aspect of the invention, there is provided a hair treatment which comprises the following two ingredients (A) and (B):

(A) Polyphenol compound: 0.001–5.0 wt%
(B) Chelating agent: 0.01–5.0 wt%

According to another aspect of the invention, there is also provided a hair treatment which comprises, in addition to the ingredients (A) and (B), the third ingredient (C):

(c) At least one decomposition derivative of keratin material selected from the group consisting of (1) hydrolysates of keratin material, (2) alkali salts of decomposition products obtained by oxidation of keratin material, and (3) alkali salts of derivatives at the thiol groups of decomposition products obtained by reduction of keratin material: 0.05–10.0 wt%

DETAILED DESCRIPTION OF THE INVENTION AND PREFERRED EMBODIMENTS

The polyphenol compounds which are the (A) ingredient of the present invention include, for example, fluoroglucinol and its derivatives such as aspidin, aspidinol and the like, tannin drugs obtained from mimosa, quebracho, cutch, gambir-catechu, Japanese gall, nutgall, arnica, coltsfoot, chamomille, common lime, hamamelis, horse chestnut, mallow, rhubarb, sage, Saint John's Bread (carob), marshmallow, birch, peach, oak and the like, tannin and its derivatives such as pyrogallol tannin, catechol tannin and the like, among which tannins are preferable.

This (A) ingredient is admixed in the hair treatment composition in an amount of 0.001–5.0 wt% (hereinafter referred to simply as %), preferably 0.005–0.1%.

The chelating agents to be the (B) ingredient of the present invention are exemplified as follows.

(1) Phosphates such as pyrophosphates, tripolyphosphates, metaphosphates, hexametaphosphates, phytates and the like.

(2) Salts of amino acids such as aspartic acid, glutamic acid, glycine and the like.

(3) Aminopolyacetates such as nitrilotriacetates, iminodiacetates, ethylenediaminetetracetates, diethylenetriaminepentacetates, glycoletherdiaminetetracetates, hydroxyethyliminodiacetates, triethylenetetraminehexacetates, djenkolates and the like.

(4) Water-soluble polymer compounds such as polyacrylates.

(5) Salts of hydroxycarboxylic acids such as glycollic acid, malic acid, hydroxypivalic acid, tartaric acid, citric acid, lactic acid, gluconic acid, mucic acid, glucuronic acid, dialdehyde starch oxide and the like, and salts of itaconic acid, methylsuccinic acid, 3-methylglutaric acid, 2,2-dimethylmalonic acid, maleic acid, fumaric acid, glutamic acid, 1,2,3,-propanetricarboxylic acid, aconitic acid, 3-butene-1,2,3,-tricarboxylic acid, butane-1,2,3,4-tetracarboxylic acid, ethanetetracarboxylic ethenetetracarboxylic acid, n-alkenylaconitic acid, 1,2,3,4-cyclopentanetetracarboxylic acid, phthalic acid, trimesic acid, hemimellitic acid, pyromellitic acid, benzenehexacarboxylic acid, tetrahydrofuran-1,2,3,4-tetracarboxylic acid, tetrahydrofuran-2,2,5,5-tetracarboxylic acid and the like.

The (B) ingredient may be in the form of either a salt or an acid and when salts are used, alkali metal salts are preferably used.

Among the above-mentioned compounds, preferable compounds as the (B) ingredient include aminopolyacetic acids or their salts, of which ethylenediaminetetracetic acid and its alkali metal salts are most preferable.

The (B) ingredient is used in an amount of 0.01–5.0%, preferably 0.05–0.5% of the hair treatment composition.

The keratin decomposition derivatives to be (C) ingredient used in the second embodiment of the invention can be prepared by the following methods: a method of hydrolyzing keratin materials; a method of decomposing keratin materials by oxidation and converting decomposed products into alkali salts; and a method of decomposing keratin materials by reduction, chemically modifying the thiol groups to give derivatives, and converting them into alkali salts.

The starting keratin materials (hereinafter referred to as "keratin") include, for examples, animal hairs, human hair, feathers, nails, horns, hooves, scales and the like, of which wool, human hair and feathers are preferable. These materials may be subjected to the oxidation or reduction reaction as they are, but if necessary, they may be cut or reduced into pieces having a suitable size or subjected to pretreatments such as washing and defatting.

The decomposition of keratin materials is conducted by any methods which follow.

(1) Hydrolysis Reaction (1) Hydrolysis with acid

Mentioned as acid are, for example, inorganic acids such as hydrochloric acid, sulfuric acid, phosphoric acid, nitric acid, hydrobromic acid and the like, and organic acids such as acetic acid, formic acid, oxalic acid and the like.

The products obtained by the hydrolysis with acids undergo the hydrolysis only at the polypeptide chains of keratin without involving any other changes, so that they show better results than products obtained by hydrolysis with alkalis.

(2) Hydrolysis with alkali

As alkali there are used inorganic alkalis such as sodium hydroxide, potassium hydroxide, lithium hydroxide, barium hydroxide, sodium carbonate, potassium carbonate, lithium carbonate, sodium silicate, borax and the like.

(3) Hydrolysis with enzyme

Examples of enzymes include acidic proteinases such as pepsin, protease A, protease B and the like, and neutral proteinases such as papain, promeline, thermolycin, trypsin, pronase, chymotrypsin and the like.

The hydrolysates obtained from enzymes show a narrower distribution of molecular weight than hydrolysates obtained using acids or alkalis and contain reduced amounts of free amino acids, thus being more favorable for use as cosmetics.

The hydrolysates obtained by these hydrolysis reactions should preferably have an average molecular weight of from 200 to 5,000. This is because the adsorptivity of keratin decomposition products on hair depends on the molecular weight of the products and a product with a molecular weight of about 1000 is most ready to adsorb on hair but those having average molecular weights higher than 5,000 scarecely adsorb on hair.

The disulfide bonds in the keratin decomposition derivatives should favorably be left in amounts as great as possible. To this end, it is recommended to use a keratin material of high purity and to effect the hydrolysis reaction under mild conditions.

(2) Oxidation and Decomposition Reaction

The oxidation of keratin is carried out by various methods known per se (N. H. Leon; Textile Progress, Vol. 7, page 1 (1975)). Oxidizing agents are preferably of the type which may be either organic or inorganic but acts electrophilically on the disulfide bonds (S—S bonds) in the keratin structure. Examples of the oxidizing agents include organic peracids, inorganic peroxo acids or their salts, permanganic acid or its salts, chromic acids or related compounds, halogens, peroxides, oxyacids or their salts and the like, among which organic peracids such as peracetic acid, performic acid and perbenzoic acid are most preferable.

By this, the disulfide bonds of keratin are cleft into sulfonic acid (—SO$_3$H).

(3) Reduction Decomposition and Chemical Modification Reactions

Reducing agents employed for reducing keratin are preferably organic or inorganic reducing agents of the type which can serve to cleave the disulfide bonds in the keratin structure into thiol groups (—SH) and generally act nucleophilically on the disulfide bonds. Examples of the reducing agents include organic reducing agents such as mercaptoethanol, thioglycollic acid, benzylmercaptan, 1,4-dithiothreitol, tributylphosphine and the like and inorganic reducing agents such as sulfides which include sodium hydrogensulfite and sodium hydrosulfide, metallic hydrides which include lithium aluminium hydride.

The resulting decomposition products obtained by the reduction of keratin are then chemically modified at the thiol groups to obtain a derivative thereof (hereinafter referred to as keratin reduction derivative). The derivatives at the thiol groups include:

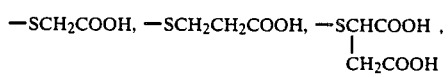

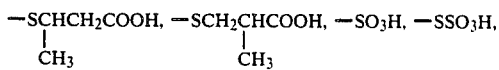

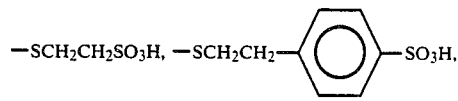

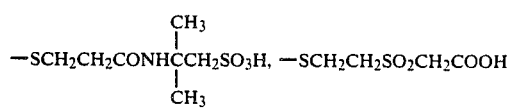

among which —SCH$_2$COOH and —SCHCOOH are preferable.
                                             |
                                             CH$_2$COOH The chemical modification of the thiol groups can be conducted on the basis of procedures known, for example, from N. H. Leon; Textile Progress, Vol. 7 (1975), "Yuki Ioo Kagobutsu (Organic Sulfur Compounds)" by Shigeru Daikyo and published by Kagaku Dojin (1968), and "Kobunshi Jikkengaku Koza (Course of Experiments of Polymers) by Masami Oku, Vol. 12, Kyoritsu Shuppan (1957).

Alkali salts of the decomposition products obtained by oxidation of keratin and reduction derivatives of keratin include inorganic alkali metal salts such as sodium, potassium and the like, ammonium salts, and salts with organic bases such as ethanolamine, diethanolamine, triethanolamine, 2-amino-2-methylpropanol, aminomercaptopropanediol, triisopropanolamine, glycine, histidine, alginine and the like. These salts may be prepared in a separate system and admixed with a hair treatment composition. Alternatively, the oxidation decomposition product or the reduction keratin derivative and an alkaline material may be admixed with a hair treatment where they are converted into a corresponding salt. Examples of the alkaline materials include inorganic alkaline materials such as sodium hydroxide, potassium hydroxide, sodium carbonate, potassium carbonate, ammonia and the like, and organic alkaline materials such as ethanolamine, diethanolamine, triethanolamine, 2-amino-2-methyl-1-propanol, 2-amino-2-methyl-1,3-propanediol, 2-amino-2-methyl-1-propanol, 2-amino-2-ethyl-1,3-propanediol, 2-amino-1-butanol, triisopropanolamine, diisopropanolamine, monoisopropanolamine, lysine, alginine, histidine, hydroxylysine and the like. These alkaline materials are preferably used in an amount of 0.1–8 equivalents with respect to the carboxyl groups or sulfonyl groups in the keratin oxidation decomposition product or the keratin reduction derivative.

The thus obtained (C) ingredients may be used singly or in combination and is employed in an amount of 0.05-10.0%, preferably 0.1-1.0%, of the total composition of the hair treatment as defined hereinbefore.

The hair treatments according to the invention can be prepared by a usual manner. That is, the hair treatments according to the first and second embodiments of the invention are prepared by dissolving the ingredients (A) and (B) and the ingredients (A), (B) and (C), respectively, into appropriate solvents, or by forming them into an emulsion, suspension or gel by the use of surface active agents.

Examples of the solvents include water, lower alcohols having 1-3 carbon atoms, propylene glycol, glycerine and the like.

The hair treatment according to the invention may be further admixed with arbitrary ingredients depending on the end use. For instance, there may be used within ranges where the effect of the hair treatments are not impeded surface active agents such as anionic active agents, cationic active agents, nonionic active agents and amphoteric agents, oils and fats such as aliphatic higher alcohols, lanolin oil, esters and liquid paraffin and the like, thickners such as hydroxyethyl cellulose, methyl cellulose, hydroxypropyl methyl cellulose and the like, preservatives perfumes and the like.

The thus obtained hair treatment can be used in the form of an aqueous solution, ethanol solution, emulsion, suspension or gel and applied in the form of known forms such as shampoo, hair rinse, hair conditioner, preshampoo, hair spray, hair brushing lotion, hair setting lotion, hair liquid, hair tonic and the like.

The present invention is particularly described by way of examples and synthetic examples, which should not be construed as limiting the invention thereto.

EXAMPLE 1

Hair treatments A, B and C of the following compositions were prepared to determine a curl-forming and retaining effect. The results are shown in Table 1. Test method:

A tress of Japanese female hairs having a weight of 5 g and a length of 20 cm was immersed in each of the hair treatments for 10 minutes, rinsed, wound about a glass tube with a diameter of 1 cm and dried with a dryer for 5 minutes. After drying, the tress was removed, and the degrees of curling and retentivity when the curled tress was allowed to stand in a room were measured.

The degree of curling was calculated from the following formula.

Degree of Curling (%) =

$$100 - \frac{\left(\begin{array}{c}\text{Length of curled tress}\\\text{immediately after its}\\\text{removal}\end{array}\right) - \left(\begin{array}{c}\text{Length of curled}\\\text{tress after } t \text{ hours}\end{array}\right)}{\left(\begin{array}{c}\text{Length of curled tress immediately}\\\text{after its removal}\end{array}\right)} \times 100$$

Composition:

|  | A | B | C |
| --- | --- | --- | --- |
| Tannin (pharmacopoeia) | 0.01(%) | 0.01(%) | —(%) |
| Disodium ethylenediaminetetracetate | 0.1 | — | 0.1 |
| Water | balance | balance | balance |

Results:

TABLE 1

| Hair Treatment | | Degree of Curling | |
| --- | --- | --- | --- |
| | | After 30 Min. | After 8 hours |
| Product of Invention | Composition A | 89 | 85 |
| Comparative Products | Composition B | 70 | 52 |
| | Composition C | 62 | 49 |
| Control (water alone) | | 61 | 43 |

EXAMPLE 2

Shampoo Composition:
(A) Triethanolamine laurylsulfate: 20.0%
(B) Lauric acid diethanolamide: 5.0
(C) Propylene glycol: 5.0
(D) Ethanol: 2.0
(E) Disodium ethylenediaminetetracetate: 0.2
(F) Tannic acid (Pharmacopeia): 0.02
(G) Water: balance Preparation: (E) was added to (G), to which was added (F), followed by complete dissolution. Thereafter, the solution was heated to 60° C., to which was added a mixed solution of (A)-(D), followed by cooling while agitation to obtain a shampoo composition.

EXAMPLE 3

Hair Conditioner Composition:
(A) Tannic acid (Pharmacopeia): 0.005%
(B) Disodium ethylenediaminetetracetate: 0.1
(C) Ethanol: 5.5
(D) Hydroxyethyl cellulose: 1.0
(E) Water: balance (A)-(E) were uniformly mixed for dissolution at room temperature to obtain the composition.

EXAMPLE 4

Hair Setting Lotion:
(A) Tannic acid (Pharmacopeia): 1.0%
(B) Disodium ethylenediaminetetracetate: 0.5
(C) Decomposition derivative obtained by oxidation of keratin (obtained in Synthetic Example 1): 1.0
(D) Ethanol: 30.0
(E) Water: balance (A)-(E) were mixed and uniformly dissolved, which was adjusted in pH to 7 using sodium hydroxide to obtain the composition.

EXAMPLE 5

Hair Rinse Composition:
(A) Stearyltrimethylammonium chloride: 1.0%
(B) Tannic acid (Pharmacopeia): 0.01
(C) Disodium ethylenediaminetetracetate: 0.2
(D) Propylene glycol: 5.0
(E) Keratin reduction derivative (Synthetic Example 2(a)): 1.0
(F) Water: balance To (F) were added (C), (B) and (E), to which was further added (A) dissolved into (D), followed by agitation to obtain the composition.

EXAMPLE 6

Hair Liquid Composition:
(A) Polyoxypropylene methyl ether: 10.0%
(B) Ethanol: 40.0
(C) Tannic acid (Pharmacopeia): 0.05
(D) Disodium ethylenediaminetetracetate: 0.1
(E) Keratin reduction derivative (Synthetic Example 2(b)): 2.0
(F) Water: balance (A)–(E) were mixed together and dissolved uniformly at room temperature to obtain the composition.

EXAMPLE 7

Hair Tonic Composition:
(A) Ethanol: 50.0
(B) l-menthol: 1.0
(C) Tannic acid: 0.1
(D) Disodium ethylenediaminetetracetate: 0.1
(E) Derivative of keratin hydrolysate (Synthetic Example 3(a)): 2.0
(F) Water: balance (A)–(F) where mixed together and uniformly dissolved at room temperature to obtain the composition.

EXAMPLE 8

Shampoo Composition:

|     |                                      | A       | B       |
| --- | ------------------------------------ | ------- | ------- |
| (A) | Sodium polyoxyethylene-(2) laurylsulfate | 15.0%   | 15.0%   |
| (B) | Coconut oil fatty acid diethanolamide | 3.5     | 3.5     |
| (C) | Sodium benzoate                      | 0.5     | 0.5     |
| (D) | Disodium ethylenediaminetetracetate  | 0.2     | 0.2     |
| (E) | Birch Extract*                       | 0.1     | —       |
| (F) | Perfume                              | 0.3     | 0.3     |
| (G) | Water                                | balance | balance |

Preparation: (A), (B), (C), (D) and (G) were mixed together and heated to about 60° C. while agitating, and after cooling, (F) and (E) were added to the mixture at about 40° C. and agitated to obtain a shampoo composition A.

*Birch Extract

This extract is that which is obtained by adding 1 part of a 40% propylene glycol aqueous solution to 2 parts of the whole plant body of Birch (*Folia betulae*) for immersion at 20°–25° C. for 10 days and then subjecting the mixture to centrifugation and filtration.

The resulting shampoo composition A of the invention and control B were used to evalutate their effect of preventing hair damage.

(Evaluation Method)

Two tresses each having a weight of 20 g were provided and were, respectively, washed with A and B, followed by drying with a hair dryer and brushing with a nylon hair brush one hundred times. The above procedure was repeated 20 times to check a number of broken hairs on each brushing and the total numbers of the broken hairs in the respective cases were compared with each other.

(Results)

The number of broken hairs in each case of the above test was found to be as follows.
Shampoo Composition A (Product of Invention): 16
Shampoo Composition B (Control): 127

As will be apparently seen from the above results, the shampoo composition A showed a better hair damage-preventing effect than the shampoo composition B.

EXAMPLE 9

Shampoo Composition:
(A) Ammonium laurylsulfate: 14.0%
(B) Diethanolamine laurate: 4.0
(C) Sodium benzoate: 0.5
(D) Ammonium chloride: 0.2
(E) Citric acid: 0.3
(F) Carob extract*: 0.2
(G) Perfume: 0.3
(H) Water: balance Preparation: (A), (C), (E) and (H) were mixed together and heated to about 60° C. with agitation, to which was added (B) of the same temperature. After cooling, (F) and (G) were added at about 40° C. and finally (D) was added, followed by agitating to obtain a shampoo composition.

*Carob Extract

This extract is obtained by roasting an outercover of Saint John's Bread (Carob Beans) and subjected to solvent extraction with 50% alcohol, followed by centrifugation and filtration and then concentrating under vacuum to an extent that a dried residue (solid matters) was contained in about 85%.

SYNTHETIC EXAMPLE 1

Preparation of Decomposition Derivative by Oxidation of Keratin:

(a) Ten grams of wool fibers were immersed in 700 g of an aqueous 8% peracetic acid solution at room temperature for 1 day to conduct the oxidation reaction. The resulting oxidized wool fibers were filtered, washed with water and immersed in 700 g of a 0.1N ammoniacal solution at room temperature for one day, permitting about 90% of the wool to dissolve in the ammoniacal solution. About 1 g of the insoluble matters were removed by filtration and the aqueous ammoniacal solution of keratose to be an oxidation decomposition product of the wool keratin was admixed with 2N hydrochloric acid to adjust its pH to 4.0, whereupon α-keratose was settled as a precipitate. This precipitate was filtered, washed with acetone and dried to obtain 5.4 g of 60-keratose.

SYNTHETIC EXAMPLE 2

Preparation of Reduction Decomposition Derivatives of Keratins:

(a) Ten grams of wool fibers were immersed in 600 ml of an aqeous solution with concentrations of 8M urea and 0.01M tris buffer, to which was added 6 ml of 2-mercaptoethanol, followed by adjusting the pH to 10 by means of a 5N potassium hydroxide aqueous solution to conduct the reduction reaction in a stream of nitrogen at room temperature. About 3 hours after commencement of the reaction, the wool dissolved in the reaction solution in an amount of about 85% thereof. While the system was adjusted with a 5N potassium hydroxide solution to that the pH was not below 7, 16.5 g of iodoacetic acid was gradually added and the pH of the system was adjusted finally to 8.5 to carry out the carboxymethylation reaction at room temperature for 2 hours. The reaction solution was filtered to remove insoluble matters therefrom and the resultant filtrate was charged into a cellulose tube wherein it was dialyzed against ion-exchanged water to remove low molecular weight impurities including urea. As the urea was dialyzed, the content in the cellulose tube became cloudy since HGT (components with high contents of glycine and tyrosine) to be water-insoluble matters was caused to precipitate. After completion of the dialysis, the HGT was centrifuged and S-carboxymethyl keratin (SCMKA) was obtained from the neutral transparent solution of SCMKA by the isoelectric precipitation method. That is, 1N hydrochloric acid was added to the system to adjust its pH to 4.4 by which SCMKA became insoluble and separated as precipitate. This precipitate was filtered, washed with ethanol and dried to obtain 4.2 g of SCMKA.

(b) The procedure of Synthetic Example 2(a) was repeated except that there used instead of wool fibers feathers which were heated for 6 minutes in an autoclave by means of a superheated steam of 6 kg/cm$^2$ and 240° C. and then abruptly released in the air to obtain a porous puffed product and that 1.75 g of maleic acid was used instead of iodoacetic acid, thereby obtaining 5.3 g of S-(1,2-dicarboxyethyl)-keratin.

SYNTHETIC EXAMPLE 3

Preparation of Hydrolysis Derivative of Keratin:

(a) Ten grams of wool fibers were immersed in 300 g of a 1% sodium hydrogensulfite aqueous solution, whose pH was adjusted to 6.7 by means of a 5N aqueous caustic soda solution. Thereafter, 0.2 g of papain was added to the system to conduct the hydrolysis reaction at 60° C. for 15 hours, by which about 80% of the wool dissolved. Insoluble matters were removed by filtration and the sulfite contained in the resulting filtrate was removed by a ultrafiltration technique using a membrane with a fractional molecular weight of 500. The aqueous solution of the hydrolysate was concentrated and freeze dried to obtain 7.7 g of the hydrolysate having a molecular weight of 500-2000.

What is claimed is:

1. In an improved hair treatment composition for restoring the flexibility and/or resilience of the hair where the improvement consists essentially of the following two ingredients (A) and (B):
   (A) tannic acid 0.001–5.0 wt%
   (B) ethylene diamine tetracetic acid: 0.01–5.0 wt%.

2. The hair treatment composition of claim 1 further comprising:
   (C) At least one decomposition derivative of keratin material selected from the group consisting of (1) hydrolysates of keratin material, (2) alkali salts of decomposition products obtained by oxidation of keratin material, and (3) alkali salts of derivatives at thiol groups of decomposition products obtained by reduction of keratin material: 0.05–10.0 wt%.

3. The composition of claim 1 wherein the tannic acid is present in an amount between about 0.005–0.1 wt%.

4. The composition of claim 1, wherein the chelating agent is in the form of a salt thereof.

5. The composition of claim 4 wherein the salts are alkali metal salts.

6. The composition of claim 1, wherein the chelating agent is present in an amount of between about 0.05 and 0.5 wt %.

7. The composition of claim 2, wherein the keratin hydrolysate has an average molecular weight of between about 200 and 5,000.

8. The composition of claim 7, wherein the average molecular weight of the hydrolyzate of keratin is at least 1,000.

9. The composition of claim 2 wherein the ingredient (c) is present in an amount between bout 0.1 and 1.0% wt %.

10. The composition of claim 1 further comprising a solvent selected from the group consisting of water, $C_1$–$C_3$ alcohols, propylene glycol and glycerine.

11. The composition of claim 1 in the form of a solution, emulsion suspension or gel.

12. The composition of claim 1, further comprising an additive selected from the group consisting of:
   (a) a surface active agent;
   (b) oils, fats;
   (c) thickeners;
   (d) preservatives; and
   (e) perfumes.

13. The composition of claim 1 in the form of a shampoo, hair rinse, hair conditioner, preshampoo, hair spray, hair brushing lotion, hair setting lotion, hair liquid and hair tonic.

* * * * *